United States Patent [19]

Hinsken et al.

[11] 4,440,887
[45] Apr. 3, 1984

[54] 4-AMINOMETHYLPOLYALKYLPIPERI-DINES USEFUL AS LIGHT STABILIZERS

[75] Inventors: Hans Hinsken, Kandern, Fed. Rep. of Germany; Wolfgang Mueller, Allschwil, Switzerland; Hermann Schneider, Grenzach-Wyhlen, Fed. Rep. of Germany

[73] Assignee: Sandoz Ltd., Basel, Switzerland

[21] Appl. No.: 341,614

[22] Filed: Jan. 22, 1982

[30] Foreign Application Priority Data

Jan. 28, 1981 [DE] Fed. Rep. of Germany ....... 3102718

[51] Int. Cl.$^3$ ..................... C07D 211/48; C08K 5/34; C09D 3/81
[52] U.S. Cl. ...................................... 524/99; 428/460; 523/351; 524/103; 525/162; 546/188; 546/242
[58] Field of Search ................... 524/96, 97, 99, 103, 524/100; 544/198; 546/188, 242

[56] References Cited

U.S. PATENT DOCUMENTS

| | | | |
|---|---|---|---|
| 3,937,711 | 2/1976 | Cook | 524/103 |
| 4,064,102 | 12/1977 | Hillard et al. | 524/99 |
| 4,118,368 | 10/1978 | Soma et al. | 524/99 |
| 4,191,683 | 3/1980 | Brunetti et al. | 544/198 |
| 4,239,891 | 12/1980 | Wiezer et al. | 524/103 |
| 4,256,627 | 3/1981 | Moser et al. | 260/45.75 |
| 4,278,590 | 7/1981 | Dexter et al. | 524/103 |
| 4,321,374 | 3/1982 | Morimura et al. | 544/198 |
| 4,344,876 | 8/1982 | Berner | 524/100 |

OTHER PUBLICATIONS

Noller, Chemistry of Organic Compounds, second ed., 1957, pp. 230 and 254.

*Primary Examiner*—John Kight, III
*Assistant Examiner*—R. A. White
*Attorney, Agent, or Firm*—Gerald D. Sharkin; Richard E. Vila; Frederick H. Weinfeldt

[57] ABSTRACT

Compounds of formula I

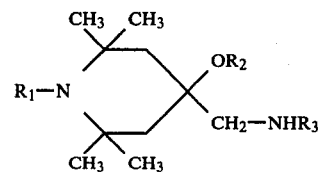

where $R_1$, $R_2$ and $R_3$ are defined in the text, are useful as light stabilizers for polymeric materials, particularly for thermoplastic polymers and automotive finishes. Preferred compounds are those in which $R_1$ is hydrogen and $R_2$ and $R_3$ are identical ($C_{8-17}$alkyl)carbonyl groups.

20 Claims, No Drawings

4-AMINOMETHYLPOLYALKYLPIPERIDINES USEFUL AS LIGHT STABILIZERS

This invention relates to 4-aminomethylpolyalkylpiperidines, which are useful as light stabilizers for polymeric materials.

The invention provides compounds of formula I

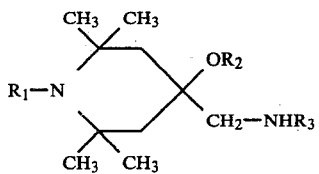

in which $R_1$ is hydrogen or $C_{1-8}$alkyl;

$R_2$ is hydrogen, ($C_{1-22}$alkyl)carbonyl, phenyl ($C_{1-4}$alkyl)carbonyl, cyclohexylcarbonyl, phenylcarbonyl in which the phenyl ring is unsubstituted or substituted by 1 or 2 $C_{1-12}$alkyl groups having a total of not more than 18 carbon atoms, or a group of formula (a)

$$-CONHR_4 \qquad (a)$$

where $R_4$ is $C_{1-18}$alkyl unsubstituted or substituted by a $-N=C=O$ group, cyclohexyl, benzyl, phenyl, or ($C_{1-12}$alkyl)phenyl; and $R_3$ has one of the significances of $R_2$ provided that $R_3$ may be hydrogen only when $R_2$ is hydrogen, or is a group of formula (b) or (c)

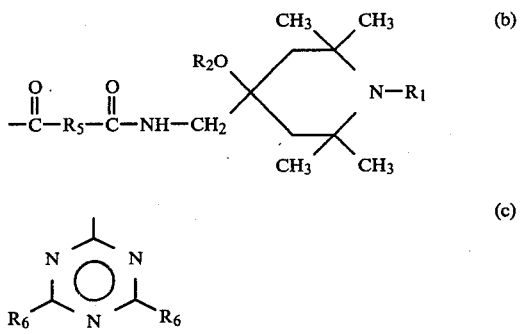

where $R_5$ is $C_{1-20}$alkylene or phenylene and
$R_6$ is a group of formula (d) or (e)

$$-NR_7R_8 \qquad (d)$$

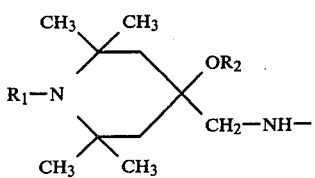

in which $R_7$ is hydrogen, $C_{1-18}$alkyl or β-hydroxyethyl, and
$R_8$ is $C_{1-18}$alkyl, β-hydroxyethyl or phenyl or $R_7$ and $R_8$ together with the nitrogen atom to which they are attached form a morpholine or piperidine group.

In compounds of formula I, wherever the same symbol appears more than once it may have the same or different significances, unless otherwise stated. All $C_3$ or higher alkyl groups may be either straight chain or branched.

$R_1$ is preferably $R_1'$ where $R_1'$ is hydrogen or methyl, and more preferably $R_1$ is hydrogen.

$R_2$ and $R_3$ as alkylcarbonyl preferably contain a $C_{1-17}$ alkyl group, more preferably a $C_{8-17}$alkyl group most preferably a $C_{11-17}$alkyl group. When $R_3$ is other than a group (b) or (c), $R_2$ and $R_3$ are preferably identical. $R_2$ preferably has one of the significances of hydrogen, alkylcarbonyl or a group of formula (a) and is preferably $R_2'$ where $R_2'$ is hydrogen, ($C_{1-17}$alkyl)carbonyl or a group of formula (a) in which $R_4$ is $R_4'$ where $R_4'$ is $C_{1-17}$alkyl or phenyl. More preferably $R_2$ is $R_2''$ where $R_2''$ is hydrogen or ($C_{8-17}$alkyl)carbonyl. Where $R_3$ is a group of formula (b) or (c) then $R_2$ is preferably hydrogen.

$R_3$ preferably has one of the significances of alkylcarbonyl, a group of formula (a) or a group of formula (b).

$R_3$ is preferably $R_3'$ where $R_3'$ is ($C_{1-17}$alkyl)carbonyl, a group of formula (a) in which $R_4$ is $R_4'$ or a group of formula (b) in which $R_1$ is hydrogen, $R_2$ is $R_2'$ and $R_5$ is $R_5'$ where $R_5'$ is $C_{1-8}$alkylene or p-phenylene. More preferably, $R_3$ is $R_3''$ where $R_3''$ is ($C_{8-17}$alkyl)carbonyl or a group of formula (b) in which $R_1$ is hydrogen, $R_2$ is hydrogen and $R_5$ is $R_5'$. Most preferably $R_3$ is $R_3'''$ where $R_3'''$ is ($C_{11-17}$alkyl)carbonyl and $R_2$ and $R_3$ preferably have the same significance.

Where $R_3$ is a group of formula (b), the compound is preferably a symmetrical compound of formula $I_s$

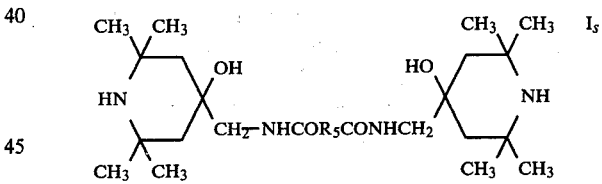

where $R_5$ is preferably $R_5'$.

Where $R_3$ is a group of formula (c), this preferably contains either 0 or 2 groups of formula (e). In group (d), $R_7$ and $R_8$ are preferably $C_{1-18}$alkyl or together with the nitrogen atom to which they are attached, form a morpholine or piperidine ring. More preferably $R_7$ and $R_8$ together form one of these two ring systems.

Preferred compounds of formula I are those of formula Ia

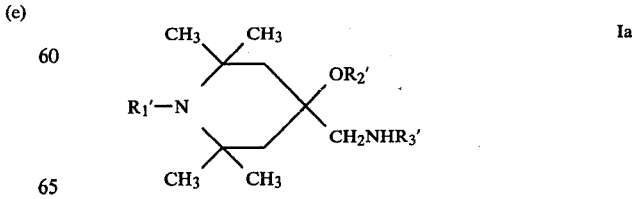

where $R_1'$, $R_2'$ and $R_3'$ are defined above, and particularly preferred compounds are those of formula Ib

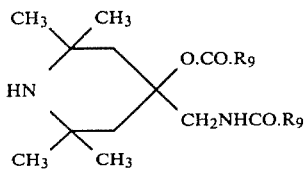
Ib

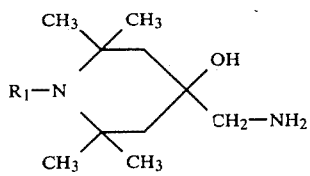

where each group $R_9$ is $C_{8-17}$alkyl and both groups $R_9$ are preferably the same.

Compounds of formula Ic

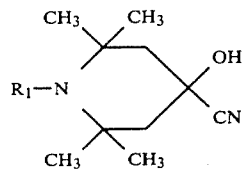
Ic that is, compounds of formula I in which both $R_2$ and $R_3$ are hydrogen, may be prepared by reduction of a compound of formula VII

VII in known manner. Reduction may be carried out for example by catalytic hydrogenation or by the use of metal hydrides, e.g. lithium aluminium hydride.

Compounds of formula Ic are themselves light-stabilizers, but are primarily of use as intermediates in the preparation of other compounds of formula I. Thus, where $R_2$ is hydrogen and $R_3$ is a group other than (a), (b) or (c), the compound of formula Ic may be reacted with 1 mole of a compound of formula III

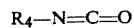
III where $R_{3a}$ has any of the significances of $R_3$ other than hydrogen (a), (b) or (c); or with a functional derivative thereof.

Compounds of formula I in which $R_2$ is hydrogen and $R_3$ is a group of formula (a) may be prepared by reacting a compound of formula Ic with 1 mole of a compound of formula IV $$R_4-N=C=O$$
IV in which $R_4$ is defined above.

Where $R_2$ is hydrogen and $R_3$ is a group of formula (b), 2 moles of the compound of formula Ic is reacted with 1 mole of a compound of formula V

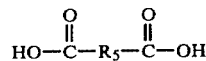
V in which $R_5$ is defined above, or with a functional derivative thereof.

Where $R_2$ is hydrogen and $R_3$ is a group of formula (c), from 1 to 3 moles of compound of formula Ic is reacted with 1 mole of a compound of formula VI

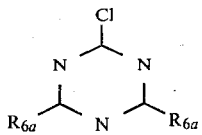
VI in which $R_{6a}$ has one of the significances of $R_6$ or is chlorine.

Compounds of formula I in which $R_2$ is other than hydrogen may be obtained by reacting the product of any of the above reactions with a further mole of a compound of formula III or a functional derivative thereof, or of formula IV. The compounds of formulae III, IV, V, VI and VII are known or may be prepared by known methods from available starting materials.

Compounds of formula I are useful as stabilizers to protect polymeric materials against degradation by light. The compounds have particularly good solubility and miscibility in solvent systems and in liquid polymers and prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20-80% by wt. of compound of formula I; or as a solid master-batch composition containing 20-80% by wt. of compound of formula I and 80-20% by wt. of a solid polymeric material which is identical with or compatible with the polymeric material to be stabilized.

Suitable polymeric materials include plastics materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastics materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, tubes, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis-[methylene-3(3', 5'-ditert.-butyl-4-hydroxyphenyl-)-propionate], 1,3,3-tris-(2-methyl-4-hydroxy-5-tert.-butylphenol)-butane, 1,3,5-tris(4-tert.-butyl-3-hydroxy-2,6-dimethylbenzyl)-1,3,5-triazin-2,4,6(1H, 3H, 5H)-trione, bis(4-tert.-butyl-3-hydroxy-2,6-dimethylbenzyl)dithiolterephthalate, tris(3,5-ditert.-butyl-4-hydroxybenzyl)isocyanurate, the triester of β-(4-hydroxy-3,5-ditert.-butylphenyl)propionic acid with 1,3,4-tris-(2-hydroxyethyl)-5-triazin-2,4,6(1H, 3H, 5H)-trione, bis[3,3-bis-(4'-hydroxy-3-tert.-butylphenyl)-butyric acid]glycol ester, 1,3,5-trimethyl-2,4,6 tris-(3,5-ditert.-butyl-4-hydroxybenzyl)benzene, 2,2'-methylene-bis-(4-methyl-6-tert.-butylphenyl)terephthalate, 4,4-methylene-bis(2,6 ditert.-butylphenol), 4,4'-butylidene-bis-(tert.-butylmeta-cresol), 4,4-thio-bis-(2-tert.-butyl-5-methylphenol), 2,2'-methylene-bis-(4-methyl-6-tert.-butylphenol).

Sulphur-containing antioxidative co-stabilizers which may be used include for example distearylthiodipropionate, dilaurylthiodipropionate, methane tetrakis(-methylene-3-hexylthiopropionate), methane tetrakis(-methylene-3-dodecylthiopropionate) and dioctadecyl-disulphide. Phosphorus-containing co-stabilizers include for example trinonylphenyl phosphite, 4,9-distearyl-3,5,8,10-tetraoxadiphosphaspiroundecane, tris-(2,4-ditert.-butylphenyl)phosphite and tetrakis(2,3-ditert.-butylphenyl)-4,4'-biphenylylene diphosphonite. Further additives such as aminoaryl compounds and UV-absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxolic acid diamides may be used. Other known types of additives, e.g. flame retardants and antistatic agents, may also be added.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 100° C., in order to harden the finish in an acceptable time once it has been applied to the primer-coated metal surface. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat is applied over a base coat containing the pigment and metal flakes. Such two-coat metallic finishes have particular need of UV stabilizers in the top coat, since the polymer in this coat is not protected by light-absorbing pigments, and it is subjected to almost double the normal amount of radiation because of reflection of light from the lower metallic layer.

The compounds of formula I are particularly useful in stoving finishes, particularly in the top coat of two-layer metallic finishes.

The compounds of formula I are suitable for use as UV stabilizers in a wide range of liquid finishes, for example those base on combinations of melamine-formaldehyde resins with oil-modified polyester resins, polyacrylate resins with added crosslinkers, or saturated polyesters; or on self-crosslinked polyacrylate or polyacrylate resin copolymerised with styrene.

Further examples are two-component finishes based on an aliphatic or aromatic di-isocyanate and a hydroxy-group-containing polyacrylate, polyester or polyether resin. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates.

The compound of formula I may be added to the finish at any stage in its manufacture, and may be added in solid form or in solution, preferably in the form of a liquid concentrate in a suitable solvent.

The addition of from 0.02–5% by weight, preferably 0.2–2% by weight of one or more compounds of formula I gives a clear improvement in the light- and weather-stability of organic pigments in stoving finishes as well as reducing the tendency to hairline cracking and loss of gloss as the result of weathering. This is surprizingly also found for metallic finishes, and excellent long-term stability of the clear top coat of two-layer metallic finishes is obtained. In such finishes, the compound of formula I may be added to the metallic undercoat, the clear top coar or both, preferably only to the clear top coat.

The following Examples, in which all parts are by weight and all temperatures in degrees Centigrade, illustrate the invention.

EXAMPLE 1

To a suspension of 40 parts 4-hydroxy-4-cyano-2,2,6,6-tetramethylpiperidine in 400 parts ether is added gradually 16.6 parts lithium aluminium hydride, keeping the temperature at 0° $\propto$ 10°. The mixture is heated to reflux for 90 minutes, then cooled to 0°–15° while 100 parts water are added dropwise. The solid precipitate is removed by filtration and the filtrate dried over sodium sulphate, filtered and the solvent evaporated. The residue is purified by chromatography on silica gel, eluting with a mixture of ethanol/concentrated aqueous ammonia in the volume ratio 5:1. The product is 4-hydroxy-4-aminomethyl-2,2,6,6-tetramethylpiperidine, m.p. 87°–89°. (Compound of formula Ic, $R_1 = H$.)

EXAMPLE 2

To a two-phase mixture of 1 part 4-hydroxy-4-aminomethyl-2,2,6,6-tetramethylpiperidine, 50 parts ether and 5.4 parts 1 N aqueous sodium hydroxide at room temperature is added dropwise 1.8 parts stearoyl chloride. The reaction mixture is shaken periodically until no more cloudiness appears in the ether layer. The organic phase is separated, dried over sodium sulphate, filtered and the solvent evaporated. The crude product is recrystallized from ethyl acetate and dried in a vacuum oven. The product consists of white crystals of the compound of formula

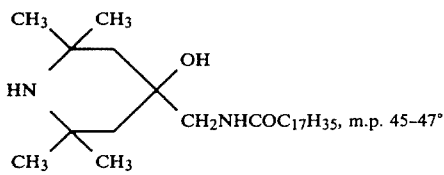

EXAMPLES 3-9

The following compounds are obtained in analogous manner by reaction of the product of Example 1 with the appropriate reagent in the appropriate molar ratio:

Example 3:

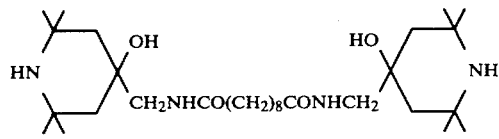

TABLE I

Compounds of formula

| Example No. | $R_2$ | $R_3$ |
|---|---|---|
| 4 | —CO—$C_{17}H_{35}$ | —CO—$C_{17}H_{35}$ |
| 5 | H | (2,6-dipiperidinyl-triazinyl) |
| 6 | —CONH—C₆H₅ | —CONH—C₆H₅ |
| 7 | —CONH—$C_{18}H_{37}$ | —CONH—$C_{18}H_{37}$ |
| 8 | H | —CONH—(CH₂)₆—N=C=O |
| 9 | H | (2-piperidinyl-6-morpholinyl-triazinyl) |

APPLICATION EXAMPLE (A)

0.5% by wt. of the compound of Example 2 is worked into polypropylene (containing no UV stabilizer) in a kneading mixer at 180°. The resulting mass is pressed into a 3 mm thick plate, and also into a 0.3 mm thick film. The film is illuminated in an Atlas Weatherometer WRC 600 with a xenon lamp, and the damage caused by UV light is measured by the growth in intensity of the IR carboxyl band absorption at 5.8μ. According to test method DIN 53453, the change in impact strength of samples cut from the 3 mm plate is measured after exposure in the Atlas Weatherometer. In both cases the results obtained are better than those using unstabilized polymer.

APPLICATION EXAMPLE (B)

A two-layer metallic finish is prepared having the following composition:

(a) Base Coat 12.6 parts commercial polyacrylate resin, with added cross-linking as defined in DIN 53 186 (Viacryl SC 344, Vianova, Vienna, supplied as 50% solution in xylene/butanol 4:1)

2.19 parts commercial butanol-etherified melamine resin, medium reactive, prepared by condensation of 1 mol melamine with 3–6 mole formaldehyde, etherified with 3–6 mole butanol according to DIN 53 187 (Maprenal MF 800, Casella, supplied as 72% solution in isobutanol)

0.96 parts butanol 0.26 parts colloidal silicic acid 7.05 parts xylene 52.0 parts of a 20% cellulose acetate butyrate solution of the following composition by weight:
  20% cellulose acetate butyrate: acetyl content 13.6%, butyryl content 38.7%, hydroxyl content 1.25%, viscosity of 20% solution in acetone = 200 cp
  10% butanol
  35% xylene
  35% butyl acetate 6.80 parts non-leafing aluminium paste, supplied as 65% suspension in alkylglycol acetate according to DIN 55 923

18.14 parts butyl acetate 0.3 parts copper phthalocyanine blue (C.I. Pigment Blue 15:1)

(b) Top Coat 80.00 parts polyacrylate resin (as in the base coat)
13.75 parts melamine resin (as in the base coat)
4.50 parts butyl glycollate
7.50 parts aromatic hydrocarbon solvent, b.p. 186°–212°
6.00 parts aromatic hydrocarbon solvent, b.p. 155°–178°

(c) Application

The base coat is applied to primer-coated metal plates by spraying, giving a layer approx. 20 μm thick, without UV stabilizer. After drying of the base coat, the plates are sprayed with (i) top coat as in (b) above, without UV stabilizer or
(ii) top coat as in (b) above, containing 1 part (i.e. 1% by wt.) of the compound of Example 2, added as an 80% solution in xylene, and stoved at 140° for 30 minutes. Exposure tests (1 year in Florida) show superior results for the plates coated with top-coat (ii).

The compounds of Examples 1 and 3–9 can be used in analogous manner to Application Examples A and B.

What is claimed is:

1. A compound of formula I

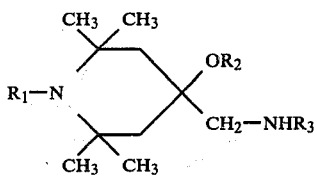

in which $R_1$ is hydrogen or $C_{1-8}$alkyl;

$R_2$ is hydrogen, ($C_{1-22}$alkyl)carbonyl, phenyl ($C_{1-4}$alkyl)carbonyl, cyclohexylcarbonyl, phenylcarbonyl in which the phenyl ring is unsubstituted or substituted by 1 or 2 $C_{1-12}$alkyl groups having a total of not more than 18 carbon atoms, or a group of formula (a)

$$-CONHR_4 \quad (a)$$

where $R_4$ is $C_{1-18}$alkyl unsubstituted or substituted by a —N=C=O group, cyclohexyl, benzyl, phenyl, or ($C_{1-12}$alkyl)phenyl; and $R_3$ is ($C_{1-22}$alkyl) carbonyl, a group of formula (a) or is a group of formula (b)

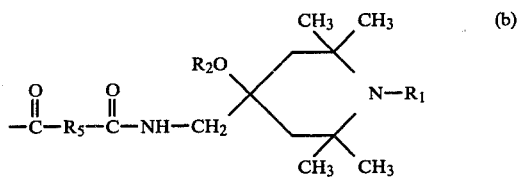

where $R_5$ is $C_{1-20}$alkylene or phenylene.

2. A compound according to claim 1 of formula $I_s$

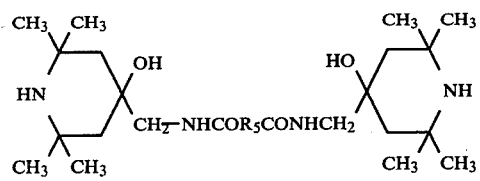

in which $R_5$ is $C_{1-8}$alkylene or p-phenylene.

3. A compound according to claim 1 of formula Ia

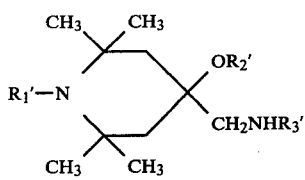

in which $R_1'$ is hydrogen or methyl, $R_2'$ is hydrogen, ($C_{1-17}$alkyl)carbonyl or a group of formula (a) in which $R_4$ is $C_{1-17}$alkyl or phenyl, and $R_3'$ is ($C_{1-17}$alkyl)carbonyl, a group of formula (a) in which $R_4$ is $C_{1-17}$alkyl or phenyl, or a group of formula (b) in which $R_1$ is hydrogen, $R_2$ is $R_2'$ and $R_5$ is $C_{1-8}$alkylene or p-phenylene.

4. A compound according to claim 3 of formula Ib

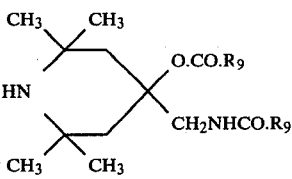

in which the $R_9$ groups are identical $C_{8-17}$alkyl groups.

5. A process for the stabilization of polymeric materials against the effect of light comprising the incorporation of from 0.01 to 5% by weight of a compound of formula I, stated in claim 1, into the polymeric material to be stabilised.

6. A polymeric material stabilized against the effects of light, containing from 0.01 to 5% by weight of a compound of formula I, stated in claim 1.

7. A solid masterbatch composition containing 20–80% by weight of a compound of formula I, stated in claim 1, and 80–20% by weight of a solid thermoplastic polymer.

8. A liquid stoving automotive finish for application to a metal surface, containing 0.02–5% by weight of a compound of formula I, stated in claim 1.

9. A cured automotive finish obtained by applying and stoving the liquid finish of claim 8.

10. A compound according to claim 1 of the formula

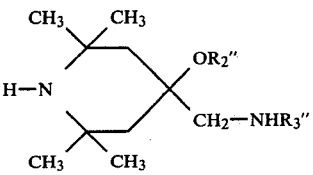

wherein $R_2''$ is hydrogen or ($C_{8-17}$alkyl)carbonyl and $R_3''$ is ($C_{8-17}$alkyl)carbonyl or a group of formula (b) in which $R_1$ and $R_2$ are hydrogen and $R_5$ is $C_{1-8}$alkylene or p-phenylene.

11. A compound according to claim 4 wherein $R_9$ is $C_{11-17}$alkyl.

12. A compound of claim 10 wherein $R_2''$ is hydrogen and $R_3''$ is —$COC_{17}H_{35}$.

13. A compound of claim 2 wherein $R_5$ is —$(CH_2)_8$—.

14. A compound of claim 4 wherein $R_9$ is —$C_{17}H_{35}$.

15. A polymeric material stabilized against the effects of light, containing 0.01 to 5% by weight of a compound according to claim 3.

16. A polymeric material stabilized against the effects of light, containing 0.02 to 1% by weight of a compound according to claim 3.

17. A composition according to claim 15 wherein the polymeric material is polyethylene, polypropylene, or ethylenepropylene copolymer, polyvinyl chloride, polyester, polyamide, polyurethane, polyacrylonitrile, ABS, an acrylate-styrene-acrylonitrile terpolymer, styrene-acrylonitrile, styrene-butadiene, polybutylene, polystyrene, chlorinated polyethylene, polycarbonate, polymethylmethacrylate, polyphenylene oxide, polypropylene oxide, a polyacetal, a phenol/formaldehyde resin or an epoxy resin.

18. A liquid stoving finish in accord with claim 8 which is a clear finish suitable for top coating over a metallic undercoat finish.

19. A liquid stoving finish of claim 18 in which the compound has the formula:

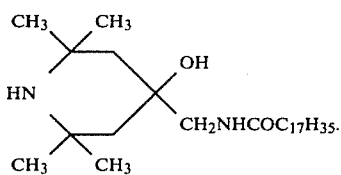

20. A composition according to claim 15 wherein the polymeric material is a combination of melamine-formaldehyde resins with oil-modified polyester resins, polyacrylate resins with added crosslinkers, or saturated polyesters; or of self-crosslinked polyacrylate or polyacrylate resin copolymerised with styrene.

* * * * *